(12) United States Patent
Pappas et al.

(10) Patent No.: US 11,253,449 B2
(45) Date of Patent: Feb. 22, 2022

(54) ORAL CARE COMPOSITIONS

(71) Applicant: Colgate-Palmolive Company, New York, NY (US)

(72) Inventors: Iraklis Pappas, Pennsauken, NJ (US); Zhichao Hu, Piscataway, NJ (US); Donghui Wu, Bridgewater, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/720,071

(22) Filed: Dec. 19, 2019

(65) Prior Publication Data
US 2020/0206109 A1    Jul. 2, 2020

Related U.S. Application Data

(60) Provisional application No. 62/785,077, filed on Dec. 26, 2018.

(51) Int. Cl.
| | | |
|---|---|---|
| *A61K 8/27* | (2006.01) | |
| *A61K 8/19* | (2006.01) | |
| *A61K 8/22* | (2006.01) | |
| *A61K 8/24* | (2006.01) | |
| *A61K 8/85* | (2006.01) | |
| *A61Q 11/00* | (2006.01) | |

(52) U.S. Cl.
CPC .............. *A61K 8/27* (2013.01); *A61K 8/19* (2013.01); *A61K 8/22* (2013.01); *A61K 8/24* (2013.01); *A61K 8/85* (2013.01); *A61Q 11/00* (2013.01)

(58) Field of Classification Search
CPC ............. A61K 8/24; A61K 8/27; A61Q 11/00
USPC ................................................... 424/49, 50
See application file for complete search history.

(56) References Cited

U.S. PATENT DOCUMENTS

| | | | | |
|---|---|---|---|---|
| 5,258,173 | A | * | 11/1993 | Waterfield ............... A61K 8/19 424/49 |
| 5,688,492 | A | * | 11/1997 | Galley .................... A61K 8/19 424/421 |
| 9,320,699 | B2 | | 4/2016 | Porter et al. |
| 10,154,948 | B2 | | 12/2018 | Vermishetti et al. |
| 10,172,770 | B2 | | 1/2019 | Rege et al. |
| 10,179,098 | B2 | | 1/2019 | Rege et al. |
| 10,195,124 | B2 | | 2/2019 | Prencipe et al. |
| 10,195,128 | B2 | | 2/2019 | Rege et al. |
| 10,226,407 | B2 | | 3/2019 | Nawrocki et al. |
| 10,258,551 | B2 | | 4/2019 | Rege et al. |
| 10,278,906 | B2 | | 5/2019 | Rege et al. |
| 10,285,919 | B2 | | 5/2019 | Rege et al. |
| 10,406,087 | B2 | | 9/2019 | Rege |
| 10,441,516 | B2 | | 10/2019 | Porter et al. |
| 10,576,029 | B2 | | 3/2020 | Rege et al. |
| 2007/0025928 | A1 | | 2/2007 | Glandorf et al. |
| 2007/0053849 | A1 | * | 3/2007 | Doyle ..................... A61K 8/21 424/50 |
| 2013/0216485 | A1 | | 8/2013 | Prencipe |
| 2015/0305993 | A1 | | 10/2015 | Rege et al. |
| 2016/0296437 | A1 | | 10/2016 | Yang et al. |
| 2017/0367939 | A1 | | 12/2017 | Thomson et al. |
| 2017/0367949 | A1 | | 12/2017 | Rege et al. |
| 2018/0168957 | A1 | | 6/2018 | Rege et al. |
| 2018/0168963 | A1 | | 6/2018 | Rege et al. |
| 2018/0168964 | A1 | | 6/2018 | Rege et al. |
| 2018/0280263 | A1 | | 10/2018 | Rege et al. |
| 2018/0280264 | A1 | | 10/2018 | Rege et al. |
| 2018/0289599 | A1 | | 10/2018 | Rege et al. |
| 2019/0110965 | A1 | | 4/2019 | Rege |
| 2019/0117542 | A1 | | 4/2019 | Rege |
| 2019/0125636 | A1 | | 5/2019 | Prencipe |
| 2019/0133903 | A1 | | 5/2019 | Vemishetti |

FOREIGN PATENT DOCUMENTS

EP          1366737        * 12/2003   ............... A61K 7/00

OTHER PUBLICATIONS

Hurlbutt et al., "Dental Caries: ApH-mediated disease." CDHA Journal—Winter 2010;pp. 9-15 (Year: 2010).*
Watson et al., 1991, "Inhibition of acid production by *Streptococcus mutans* NCTC 10449 by zinc and the effect of metal speciation," Caries Research 25:431-437, (Abstract Only).

* cited by examiner

*Primary Examiner* — Walter E Webb

(57) ABSTRACT

An oral care composition comprising primarily insoluble forms of zinc compounds and stannous compounds, as well as methods of using the same in the treatment or prevention of gingivitis, plaque, and dental caries.

20 Claims, No Drawings

ORAL CARE COMPOSITIONS

CROSS-REFERENCE TO RELATED APPLICATIONS

This application is a United States application filed under 35 U.S.C. § 119(a) claiming priority to and the benefit of U.S. Provisional Application No. 62/785,077, filed on Dec. 26, 2018, the contents of which are hereby incorporated by reference in its entirety.

FIELD

The present invention relates to an oral care composition for use in the treatment or prevention of gingivitis, plaque, and dental caries. This oral care composition comprises primarily insoluble forms of zinc compounds and stannous compounds, such as zinc oxide, zinc phosphate, stannous phosphate and stannous hydroxide.

BACKGROUND

Dental plaque is a sticky biofilm or mass of bacteria that is commonly found between the teeth, along the gum line, and below the gum line margins. Dental plaque can give rise to dental caries and periodontal problems such as gingivitis and periodontitis. Dental caries tooth decay or tooth demineralization caused by acid produced from the bacterial degradation of fermentable sugar.

Oral care compositions which contain stannous ion sources exhibit excellent clinical benefits, particularly in the reduction of gingivitis. Stannous fluoride is well known for use in clinical dentistry with a history of therapeutic benefits over forty years. However, until recently, its popularity has been limited by its instability in aqueous solutions. The instability of stannous fluoride in water is primarily due to the reactivity of the stannous ion ($Sn^{2+}$). Stannous salts readily hydrolyze at a pH above 4, resulting in precipitation from solution. It has traditionally been thought that this formation of insoluble stannous salts results in a loss of therapeutic properties.

One way to overcome the stability problems with stannous ions is to limit the amount of water in the composition to very low levels, or to use a dual phase system. Both of these solutions to the stannous ion problem have drawbacks. Low water oral care compositions can be difficult to formulate with desired rheological properties, and dual-phase compositions are considerably more expensive to manufacture and package. Thus, it is preferable to formulate a high-water composition which uses an alternative means to maintain stable efficacious stannous ion concentrations.

Soluble zinc salts, such as zinc citrate, have been used in dentifrice compositions, but have several disadvantages. Zinc ions in solution impart an unpleasant, astringent mouthfeel, so formulations that provide effective levels of zinc, and also have acceptable organoleptic properties, have been difficult to achieve. Moreover, free zinc ions may react with fluoride ions to produce zinc fluoride, which is insoluble and so reduces the availability of both the zinc and the fluoride. Finally, zinc ions can react with other dentifrice components, such as anionic surfactants (e.g. sodium lauryl sulfate), interfering with foaming and cleaning and composition stability.

Soluble metal ions, such as stannous and zinc, may also react unfavorably polymeric rheological modifiers, such as modified celluloses (e.g., carboxymethyl cellulose) and gums (e.g., xanthan gum or carrageenan gum). Such compounds often considered to be incompatible with divalent metal ions.

Traditionally, the emphasis in developing metal-ion based oral care compositions has been to maximize the concentration of soluble zinc and soluble stannous ions, because it was believed that only soluble forms of these ions contribute to antibacterial efficacy.

There remains a need for providing improved stannous ion and zinc ion containing oral care products for reducing plaque or treating or controlling gingivitis. There is also a desire for novel anti-microbial compositions that are stable in water and easy to manufacture.

BRIEF SUMMARY

Disclosed herein are oral care compositions comprising primarily insoluble stannous compounds and zinc compounds, for example, high water compositions. Methods of manufacturing such compositions, and methods of using such compositions are also described throughout. The compositions disclosed herein provide improved protection from demineralization and enhanced antibacterial activity compared to the prior art. In some embodiments, the insoluble zinc and insoluble stannous species are formed in situ by manufacturing the compositions using soluble zinc salts and/or soluble stannous salts. In some embodiments, the compositions are formulated to comprise less than 30% soluble stannous (as a proportion of total stannous). In some embodiments, the compositions are formulated to comprise less than 30% soluble zinc (as a proportion of total zinc). In some embodiments, the oral care composition is a toothpaste or oral gel composition.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

DETAILED DESCRIPTION

The following description of the preferred embodiment(s) is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight of the entire composition. The amounts given are based on the active weight of the material.

As used herein throughout, the terms "soluble" and "solubility" refer to aqueous solubility (i.e., the solubility of the described species in water). As used herein, the term "soluble" refers to a compound having a solubility product constant ($K_{SP}$) in water of greater than or equal to $1 \times 10^{-10}$ (at 20° C.). As used herein, the term "insoluble" refers to a compound having a solubility product constant ($K_{SP}$) in water of less than $1 \times 10^{-10}$ (at 20° C.).

Insoluble zinc compounds include, but are not limited to, zinc oxide, zinc phosphate, zinc pyrophosphate, zinc silicate, zinc oleate, zinc hydroxide, zinc carbonate, zinc peroxide and zinc sulfide. By way of comparison, soluble zinc compounds include zinc citrate, zinc chloride, zinc lactate, zinc nitrate, zinc acetate, zinc gluconate, zinc glycinate and zinc sulfate.

Insoluble stannous compounds include, but are not limited to, stannous phosphate (i.e., stannous orthophosphate), stannous pyrophosphate, stannous oxide, stannous sulfate, stannous peroxide, and stannous hydroxide. By way of comparison, soluble stannous compounds include stannous fluoride, stannous chloride, stannous nitrate and stannous sulfate.

In some embodiments, the present compositions are formulated by combining a soluble stannous compound or soluble zinc compound with a precipitating agent to cause an aqueous-phase exchange reaction which results in the formation and precipitation of the corresponding insoluble stannous compound or insoluble zinc compound. For example, a composition can be formulated by combining stannous fluoride (soluble) with sodium phosphate (soluble) to form stannous phosphate (insoluble). In any such case, the precipitating agent is an inorganic water-soluble salt chosen such that the anion of the salt (the "precipitating anion") corresponds to the anion of the desired insoluble stannous compound or insoluble zinc compound. In some embodiments, the soluble stannous compound or soluble zinc compound is combined with the precipitating agent in a molar ratio of about 0.5:1 to about 2:1 based on the molar amounts of metal ion and precipitating anion. For example, stannous fluoride ($SnF_2$) and sodium phosphate ($Na_3PO_4$) may be combined in about a 0.5:1 to about 2:1 molar ratio of $Sn^{2+}$ to $PO_4^{3-}$. In preferred embodiments, the soluble stannous compound or soluble zinc compound is combined with the precipitating agent in a molar ratio corresponding to the molar ratio of metal ion to precipitating anion in the desired insoluble salt. For example, stannous fluoride ($SnF_2$) and sodium phosphate ($Na_3PO_4$) may be combined in about a 3:2 (1.5:1) molar ratio of $Sn^{2+}$ to $PO_4^{3-}$ in order to yield one molar equivalent of stannous phosphate ($Sn_3(PO_4)_2$). Generally, the divalent metal ion ($M^{2+}$) may be combined with any anion (e.g., $A^-$, $A^{2-}$, $A^{3-}$, $A^{4-}$) in a molar ratio of about 0.5:1, about 1:1, about 1.5:1 or about 2:1, to form an insoluble salt having the formula $MA_2$, $MA$, $M_3A_2$, or $M_2A$, depending on the valency of the anion. Preferably, the soluble stannous compound or soluble zinc compound is combined with the precipitating agent in a "pre-mix," i.e., the two agents are combined in an aqueous mixture prior the addition of other oral care ingredients to the mixture, or prior to the mixture (after providing sufficient time for the exchange reaction to complete) is added to other components of the oral care composition.

In some embodiments, the precipitating agent is any soluble basic compound added in an amount to raise the pH of the composition to 7.0 or above. At a pH of 7.0 or above, stannous ions and zinc ions will generally precipitate as their oxide and/or hydroxide forms. In such embodiments, the soluble stannous compound or soluble zinc compound may be combined with one or more other oral care ingredients in a high-water composition to yield an intermediate composition to which the soluble basic compound is then added to cause precipitation of the desired insoluble stannous or zinc compound (e.g., stannous oxide or hydroxide and/or zinc oxide or hydroxide).

It has been surprisingly found that a high-water oral care composition comprising primarily insoluble stannous compounds and compounds resulted in improved antibacterial efficacy and improved rheological stability compared to similar compositions comprising primarily soluble stannous compounds and zinc compounds.

As used herein, the term "high water" refers to an oral care composition, such as a toothpaste or oral gel, which comprises from 10% to 99% water, by weight of the composition. For example, the composition may comprise at least 10%, 15%, 20%, 25%, 30%, 35% or 40% water, up to a maximum of, for example, 60%, 70%, 80%, 90%, 95% or 99% water, by weight of the composition. As used herein, amounts of water refer to water added directly to the composition, as well as water added as part of ingredients or components which are added as aqueous solutions. In some embodiments, the composition comprises 10-60% water, or 10-50% water, or 10-40% water, or 10-30% water, or 15-30% water, or 20-30% water, or about 25% water, by weight of the composition.

In one aspect, the present disclosure therefore provides an oral care composition (Composition 1), e.g., a high-water oral care composition, comprising an orally acceptable carrier, an insoluble stannous compound, and an insoluble zinc compound. In further embodiments of this aspect, the present disclosure provides:

1.1 Composition 1, wherein the composition comprises less than 30% soluble stannous as a fraction of total stannous by weight, and less than 30% soluble zinc as a fraction of total zinc by weight.

1.2 Composition 1 or 1.1, wherein the insoluble zinc compound is selected from one or more of zinc oxide, zinc phosphate, zinc pyrophosphate, zinc silicate, zinc oleate, zinc hydroxide, zinc carbonate, zinc peroxide and zinc sulfide.

1.3 Composition 1 or 1.1 or 1.2, wherein the insoluble zinc compound is selected from zinc oxide, zinc phosphate, and zinc pyrophosphate.

1.4 Any preceding composition wherein the insoluble stannous compound is selected from one or more of stannous phosphate, stannous pyrophosphate, stannous oxide, stannous sulfate, stannous peroxide, and stannous hydroxide.

1.5 Composition 1.3, wherein the insoluble stannous compound is selected from stannous phosphate and stannous pyrophosphate.

1.6 Any preceding composition, wherein the composition is formulated by combining a soluble stannous compound with a precipitating agent to form the insoluble stannous compound during manufacture of the composition.

1.7 Composition 1.6, wherein the soluble stannous compound is stannous fluoride or stannous chloride, or a combination thereof 1.8 Composition 1.6 or 1.7, wherein the precipitating agent is a water-soluble alkali metal or alkaline earth metal corresponding to the anion of the insoluble stannous compound (e.g., sodium hydroxide, potassium hydroxide, sodium phosphate, potassium phosphate).

1.9 Composition 1.6, 1.7 or 1.8, wherein the composition is formulated by combining the soluble stannous compound and the precipitating agent in about a 0.5:1 to 2:1 molar ratio, measured by the molar amount of stannous ion to precipitating anion, e.g., about 0.5:1, about 1:1, about 1.5:1 or about 2:1 molar ratio.

1.10 Any preceding composition, wherein the composition is formulated by combining a soluble zinc compound with a precipitating agent to form the insoluble zinc compound during manufacture of the composition.

1.11 Composition 1.9, wherein the soluble zinc compound is zinc chloride, zinc sulfate, zinc lactate, or zinc citrate, or a combination thereof 1.12 Composition 1.9 or 1.10, wherein the precipitating agent is a water-soluble alkali metal or alkaline earth metal corresponding to the anion of the insoluble zinc compound (e.g., sodium hydroxide, potassium hydroxide, sodium phosphate, potassium phosphate).

1.13 Composition 1.10, 1.11 or 1.12, wherein the composition is formulated by combining the soluble zinc compound and the precipitating agent in about a 0.5:1 to 2:1 molar ratio, measured by the molar amount of zinc ion to precipitating anion, e.g., about 0.5:1, about 1:1, about 1.5:1 or about 2:1 molar ratio.

1.14 Any of compositions 1.6 or 1.7 wherein the soluble zinc compound and/or the soluble stannous compound is pre-mixed with the precipitating agent in an aqueous solution prior to the addition of other oral care ingredients.

1.15 Any preceding composition, wherein the composition comprises the insoluble zinc compound in an amount of from 0.05 to 10% by weight, relative to the weight of the oral care composition, for example, from 0.1 to 8% by weight, or from 0.5 to 5% by weight, or from 0.5 to 4% by weight, or from 1 to 4%, or from 1 to 3% by weight, or from 2 to 3% by weight, or about 1% or about 2%, or about 2.25% or about 2.5%, by weight.

1.16 Any preceding composition, wherein the composition comprises the insoluble stannous compound in an amount of from 0.05 to 10% by weight, relative to the weight of the oral care composition, for example, from 0.1 to 8% by weight, or from 0.5 to 5% by weight, or from 0.5 to 4% by weight, or from 1 to 4%, or from 1 to 3% by weight, or from 2 to 3% by weight, or about 1% or about 2%, or about 2.25% or about 2.5%, by weight.

1.17 Any preceding composition, wherein the amount of the water is 10% by weight or more, relative to the weight of the oral care composition, for example, 10-90%, or 10-80%, or 10-70%, or 10-60%, or 10-50%, or 10-40%, or 10-30%, or 15-30%, or 20-30%, or about 25%, by weight of the composition.

1.18 Any preceding composition, wherein the composition comprises less than 30% soluble stannous by weight of total stannous, e.g., 1 to 25%, or 1 to 20%, or 1 to 15%, or 5 to 25%, or 5 to 20%, or 5 to 15%, or 10 to 25%, or 10 to 20%, or 10 to 15%, by weight of total stannous.

1.19 Any preceding composition, wherein the composition comprises less than 30% soluble zinc by weight of total zinc e.g., 1 to 25%, or 1 to 20%, or 1 to 15%, or 5 to 25%, or 5 to 20%, or 5 to 15%, or 1 to 10%, or 1 to 5%, or 5 to 10%, by weight of total zinc.

1.20 Any preceding composition, wherein the composition provides from 100 to 20,000 ppm of total stannous, e.g., from 500 to 15,000 ppm, or from 1000 to 12,000 ppm, or from 2000 to 10,000 ppm, or from 5,000 to 10,000 ppm, or from 8,000 to 10,000 ppm.

1.21 Any preceding composition, wherein the composition provides from 100 to 20,000 ppm of total zinc, e.g., from 500 to 15,000 ppm, or from 1000 to 12,000 ppm, or from 2000 to 10,000 ppm, or from 5,000 to 10,000 ppm, or from 8,000 to 10,000 ppm.

1.22 Any preceding composition wherein the composition further comprises a polymeric rheological modifier, for example, an anionic polymer or a neutral polymer.

1.23 Composition 1.22, wherein the anionic polymer is selected from the group consisting of polysaccharide gums (e.g., gellan gum, gum tragacanth, gum Arabic, sulfated carrageenan gums, alginic acid), synthetic anionic polymeric polycarboxylates, polyacrylic acids, polyphosphonic acids, and cross-linked carboxyvinyl copolymers, and/or the neutral polymer is selected from modified celluloses (e.g., methyl cellulose, hydroxyethyl cellulose, hydroxypropyl cellulose, hydroxypropyl methyl cellulose), polysaccharide gums (e.g., non-sulfated carrageenans, xanthan gum, guar gum) and polyvinyl pyrrolidone.

1.24 Composition 1.22, wherein the composition comprises an anionic polymeric polycarboxylate.

1.25 Composition 1.24, wherein the anionic polymeric polycarboxylate is selected from a modified cellulose polymer (e.g., a carboxymethyl cellulose) or a gum.

1.26 Any of Compositions 1.22-1.25, wherein the polymeric rheological modifier is present in an amount of 1 to 20% by weight of the composition, e.g., from 5 to 20%, or from 8 to 15%, or from 10 to 14%, or from 11 to 13%, or about 12%, or about 6%.

1.27 Any preceding composition, further comprising an anionic surfactant.

1.28 Composition 1.27, wherein the anionic surfactant is an anionic alkyl sulfate (e.g., sodium lauryl sulfate).

1.29 Composition 1.27 or 1.28, wherein the anionic surfactant is present in an amount of 1 to 20% by weight of the composition, e.g., from 1 to 15%, or from 1 to 10%, or from 1 to 5%.

1.30 Any preceding composition, wherein the oral care composition further comprises an abrasive, for example, silica abrasives, calcium abrasives, and other abrasives as disclosed herein.

1.31 Any preceding composition, further comprising one or more humectants, as described herein, e.g., selected from sorbitol, glycerol, xylitol and propylene glycol, or combinations thereof.

1.32 Any preceding composition, further comprising one or more cationic, nonionic or zwitterionic surfactants, as described herein, e.g., cocamidopropyl betaine, or combinations thereof 1.33 Any preceding composition, further comprising an effective amount of one or more alkali phosphate salts for example orthophosphates, pyrophosphates, tripolyphosphates, tetraphosphates or higher polyphosphates.

1.34 Composition 1.32, wherein the alkali phosphate salts comprise tetrasodium pyrophosphate or tetrapotassium pyrophosphate, for example, in an amount of 0.5 to 5% by weight of the composition, e.g., 1-3%, or 1-2% or about 2% by weight, or about 2-4%, or about 3-4% or about 4% by weight of the composition.

1.35 Composition 1.32 or 1.33, wherein the alkali phosphate salts comprise sodium tripolyphosphate or potassium tripolyphosphate, for example, in an amount of 0.5 to 6% by weight of the composition, e.g., 1-4%, or 2-3% or about 3% by weight.

1.36 Any preceding composition, further comprising one or more fluoride ion sources, for example, a fluoride ion source selected from stannous fluoride, sodium fluoride, potassium fluoride, sodium monofluorophosphate, sodium fluorosilicate, ammonium fluorosilicate, amine fluoride, ammonium fluoride, and combinations thereof.

1.37 Composition 1.36, wherein the fluoride source is stannous fluoride, optionally in an amount of 0.05-2% by weight of the composition, e.g., about 0.45%.

1.38 Any preceding composition, wherein the oral care composition is a dentifrice (e.g., a toothpaste or oral gel), powder (e.g., tooth powder), cream, strip or gum (e.g., chewing gum).

1.39 Any preceding composition, wherein the pH of the composition is from 6 to 9, such as from 7 to 9, or from 7 to 8.5, 7 to 8, or 7 to 7.5.

1.40 Composition 1.38, wherein the pH of the composition is adjusted by the addition of a suitable amount of a soluble basic compound, e.g., sodium hydroxide or potassium hydroxide.

1.41 Any preceding composition, wherein the composition is a single-phase composition (e.g., not a dual-phase composition).

1.42 Any preceding composition, wherein the composition does not comprise one or more of zinc oxide, zinc citrate, zinc lactate, or zinc phosphate.

1.43 Any preceding composition, wherein the composition does not comprise one or more of stannous fluoride or stannous chloride.

1.44 Any of the preceding compositions, wherein the composition is effective upon application to the oral cavity, e.g., by rinsing, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing and/or malodor producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity, (xiv) prevents stains and/or whiten teeth, (xv) immunize the teeth against cariogenic bacteria, (xvi) reduce or prevent oral malodor, and/or (xvii) promote systemic health, including cardiovascular health, e.g., by reducing potential for systemic infection via the oral tissues.

1.45 Any preceding composition, wherein the composition has enhanced stannous ion stability (e.g., compared to a composition comprising soluble stannous and soluble zinc compounds).

In another aspect, the present disclosure provides oral care composition (Composition 2), e.g., a high-water oral care composition, made by combining an insoluble stannous compound and an insoluble zinc compound in an orally acceptable carrier. In further embodiments, of this aspect, the present disclosure provides:

2.1 Composition 2, wherein the insoluble stannous compound is formed by first combining a soluble stannous compound with a precipitating agent in an aqueous solution for a sufficient amount of time to form the insoluble stannous compound.

2.2 Composition 2.1, wherein the composition is made by combining the resulting aqueous suspension of the insoluble stannous compound with the orally acceptable carrier.

2.3 Composition 2.1, wherein the composition is made by obtaining the insoluble stannous compound from the resulting aqueous suspension, e.g., by drying, evaporating or lyophilizing the suspension, and combining the obtained insoluble stannous compound with the orally acceptable carrier.

2.4 Composition 2, wherein the insoluble stannous compound is formed by first combining a soluble stannous compound with an orally acceptable carrier and then adding a water-soluble base in a suitable amount to raise the pH of the composition above 7.0 (e.g., to 7.0 to 9.0, or 7.0 to 8.5, or 7.0 to 8.0, or 7.0 to 7.5) causing the precipitation of stannous compound in the composition.

2.5 Composition 2 or any of 2.1-2.4, wherein the insoluble zinc compound is formed by first combining a soluble zinc compound with a precipitating agent in an aqueous solution for a sufficient amount of time to form the insoluble zinc compound.

2.6 Composition 2.5, wherein the composition is made by combining the resulting aqueous suspension of the insoluble zinc compound with the orally acceptable carrier.

2.7 Composition 2.5, wherein the composition is made by obtaining the insoluble zinc compound from the resulting aqueous suspension, e.g., by drying, evaporating or lyophilizing the suspension, and combining the obtained insoluble zinc compound with the orally acceptable carrier.

2.8 Composition 2 or any of 2.1-2.4, wherein the insoluble zinc compound is formed by first combining a soluble zinc compound with an orally acceptable carrier and then adding a water-soluble base in a suitable amount to raise the pH of the composition above 7.0 (e.g., to 7.0 to 9.0, or 7.0 to 8.5, or 7.0 to 8.0, or 7.0 to 7.5) causing the precipitation of stannous compound in the composition.

2.9 Composition 2, wherein the composition is formed by adding both an insoluble stannous compound and an insoluble zinc compound to an orally acceptable carrier, e.g., without the use of a soluble stannous compound or soluble zinc compound to form the insoluble stannous compound or insoluble zinc compound, respectively.

2.10 Any preceding composition, wherein the composition comprises less than 30% soluble stannous as a fraction of total stannous by weight, and less than 30% soluble zinc as a fraction of total zinc by weight.

2.11 Any preceding composition, wherein the insoluble zinc compound is selected from one or more of zinc oxide, zinc phosphate, zinc pyrophosphate, zinc silicate, zinc oleate, zinc hydroxide, zinc carbonate, zinc peroxide and zinc sulfide.

2.12 Any preceding composition, wherein the insoluble zinc compound is selected from zinc oxide, zinc phosphate, and zinc pyrophosphate.

2.13 Any preceding composition, wherein the insoluble stannous compound is selected from one or more of stannous phosphate, stannous pyrophosphate, stannous oxide, stannous sulfate, stannous peroxide, and stannous hydroxide.

2.14 Any preceding composition, wherein the insoluble stannous compound is selected from stannous phosphate and stannous pyrophosphate.

2.15 Any of compositions 2.1-2.4, wherein the soluble stannous compound is stannous fluoride or stannous chloride, or a combination thereof 2.16 Any of compositions 2.1 or 2.15, wherein the precipitating agent is a water-soluble alkali metal or alkaline earth metal corresponding to the anion of the insoluble stannous compound (e.g., sodium hydroxide, potassium hydroxide, sodium phosphate, potassium phosphate).

2.17 Composition 2.16, wherein the composition is formulated by combining the soluble stannous compound and the precipitating agent in about a 0.5:1 to 2:1 molar ratio, measured by the molar amount of stannous ion to precipitating anion, e.g., about 0.5:1, about 1:1, about 1.5:1 or about 2:1 molar ratio.

2.18 Any of Compositions 2.5-2.8, wherein the soluble zinc compound is zinc chloride, zinc sulfate, zinc lactate, or zinc citrate, or a combination thereof 2.19 Composition 2.5, wherein the precipitating agent is a water-soluble alkali metal or alkaline earth metal corresponding to the anion of the insoluble zinc compound (e.g., sodium hydroxide, potassium hydroxide, sodium phosphate, potassium phosphate).

2.20 Composition 2.19, wherein the composition is formulated by combining the soluble zinc compound and the precipitating agent in about a 0.5:1 to 2:1 molar ratio, measured by the molar amount of zinc ion to precipitating anion, e.g., about 0.5:1, about 1:1, about 1.5:1 or about 2:1 molar ratio.

2.21 Any preceding composition, wherein the composition comprises the insoluble zinc compound in an amount of from 0.05 to 10% by weight, relative to the weight of the oral care composition, for example, from 0.1 to 8% by weight, or from 0.5 to 5% by weight, or from 0.5 to 4% by weight, or from 1 to 4%, or from 1 to 3% by weight, or from 2 to 3% by weight, or about 1% or about 2%, or about 2.25% or about 2.5%, by weight.

2.22 Any preceding composition, wherein the composition comprises the insoluble stannous compound in an amount of from 0.05 to 10% by weight, relative to the weight of the oral care composition, for example, from 0.1 to 8% by weight, or from 0.5 to 5% by weight, or from 0.5 to 4% by weight, or from 1 to 4%, or from 1 to 3% by weight, or from 2 to 3% by weight, or about 1% or about 2%, or about 2.25% or about 2.5%, by weight.

2.23 Any preceding composition, wherein the amount of the water is 10% by weight or more, relative to the weight of the oral care composition, for example, 10-90%, or 10-80%, or 10-70%, or 10-60%, or 10-50%, or 10-40%, or 10-30%, or 15-30%, or 20-30%, or about 25%, by weight of the composition.

2.24 Any preceding composition, wherein the composition comprises less than 30% soluble stannous by weight of total stannous, e.g., 1 to 25%, or 1 to 20%, or 1 to 15%, or 5 to 25%, or 5 to 20%, or 5 to 15%, or 10 to 25%, or 10 to 20%, or 10 to 15%, by weight of total stannous.

2.25 Any preceding composition, wherein the composition comprises less than 30% soluble zinc by weight of total zinc e.g., 1 to 25%, or 1 to 20%, or 1 to 15%, or 5 to 25%, or 5 to 20%, or 5 to 15%, or 1 to 10%, or 1 to 5%, or 5 to 10%, by weight of total zinc.

2.26 Any preceding composition, wherein the composition provides from 100 to 20,000 ppm of total stannous, e.g., from 500 to 15,000 ppm, or from 1000 to 12,000 ppm, or from 2000 to 10,000 ppm, or from 5,000 to 10,000 ppm, or from 8,000 to 10,000 ppm.

2.27 Any preceding composition, wherein the composition provides from 100 to 20,000 ppm of total zinc, e.g., from 500 to 15,000 ppm, or from 1000 to 12,000 ppm, or from 2000 to 10,000 ppm, or from 5,000 to 10,000 ppm, or from 8,000 to 10,000 ppm.

2.28 Any preceding composition wherein the composition further comprises a polymeric rheological modifier, for example, an anionic polymer or a neutral polymer.

2.29 Composition 2.28, wherein the anionic polymer is selected from the group consisting of polysaccharide gums (e.g., gellan gum, gum tragacanth, gum Arabic, sulfated carrageenan gums, alginic acid), synthetic anionic polymeric polycarboxylates, polyacrylic acids, polyphosphonic acids, and cross-linked carboxyvinyl copolymers, and/or the neutral polymer is selected from modified celluloses (e.g., methyl cellulose, hydroxyethyl cellulose, hydroxypropyl cellulose, hydroxypropyl methyl cellulose), polysaccharide gums (e.g., non-sulfated carrageenans, xanthan gum, guar gum) and polyvinyl pyrrolidone.

2.30 Composition 2.29, wherein the composition comprises an anionic polymeric polycarboxylate.

2.31 Composition 2.30, wherein the anionic polymeric polycarboxylate is selected from a modified cellulose polymer (e.g., a carboxymethyl cellulose) or a gum.

2.32 Any of Compositions 2.28-2.31, wherein the polymeric rheological modifier is present in an amount of 1 to 20% by weight of the composition, e.g., from 5 to 20%, or from 8 to 15%, or from 10 to 14%, or from 11 to 13%, or about 12%, or about 6%.

2.33 Any preceding composition, further comprising an anionic surfactant.

2.34 Composition 2.33, wherein the anionic surfactant is an anionic alkyl sulfate (e.g., sodium lauryl sulfate).

2.35 Composition 2.33 or 2.34, wherein the anionic surfactant is present in an amount of 1 to 20% by weight of the composition, e.g., from 1 to 15%, or from 1 to 10%, or from 1 to 5%.

2.36 Any preceding composition, wherein the oral care composition further comprises an abrasive, for example, silica abrasives, calcium abrasives, and other abrasives as disclosed herein.

2.37 Any preceding composition, further comprising one or more humectants, as described herein, e.g., selected from sorbitol, glycerol, xylitol and propylene glycol, or combinations thereof.

2.38 Any preceding composition, further comprising one or more cationic, nonionic or zwitterionic surfactants, as described herein, e.g., cocamidopropyl betaine, or combinations thereof 2.39 Any preceding composition, further comprising an effective amount of one or more alkali phosphate salts for example orthophosphates, pyrophosphates, tripolyphosphates, tetraphosphates or higher polyphosphates.

2.40 Composition 2.39, wherein the alkali phosphate salts comprise tetrasodium pyrophosphate or tetrapotassium pyrophosphate, for example, in an amount of 0.5 to 5% by weight of the composition, e.g., 1-3%, or 1-2% or about 2% by weight, or about 2-4%, or about 3-4% or about 4% by weight of the composition.

2.41 Composition 2.39 or 2.40, wherein the alkali phosphate salts comprise sodium tripolyphosphate or potassium tripolyphosphate, for example, in an amount of 0.5 to 6% by weight of the composition, e.g., 1-4%, or 2-3% or about 3% by weight.

2.42 Any preceding composition, further comprising one or more fluoride ion sources, for example, a fluoride ion source selected from stannous fluoride, sodium fluoride, potassium fluoride, sodium monofluorophosphate, sodium fluorosilicate, ammonium fluorosilicate, amine fluoride, ammonium fluoride, and combinations thereof.

2.43 Composition 2.42, wherein the fluoride source is stannous fluoride, optionally in an amount of 0.05-2% by weight of the composition, e.g., about 0.45%.

2.44 Any preceding composition, wherein the oral care composition is a dentifrice (e.g., a toothpaste or oral gel), powder (e.g., tooth powder), cream, strip or gum (e.g., chewing gum).

2.45 Any preceding composition, wherein the pH of the composition is from 6 to 9, such as from 7 to 9, or from 7 to 8.5, 7 to 8, or 7 to 7.5.

2.46 Composition 2.45, wherein the pH of the composition is adjusted by the addition of a suitable amount of a soluble basic compound, e.g., sodium hydroxide or potassium hydroxide.

2.47 Any preceding composition, wherein the composition is a single-phase composition (e.g., not a dual-phase composition).

2.48 Any preceding composition, wherein the composition does not comprise, or is not formulated with, one or more of zinc oxide, zinc citrate, zinc lactate, or zinc phosphate.

2.49 Any preceding composition, wherein the composition does not comprise, or is not formulated with, one or more of stannous fluoride or stannous chloride.

2.50 Any of the preceding compositions, wherein the composition is effective upon application to the oral cavity, e.g., by rinsing, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing and/or malodor producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity, (xiv) prevents stains and/or whiten teeth, (xv) immunize the teeth against cariogenic bacteria, (xvi) reduce or prevent oral malodor, and/or (xvii) promote systemic health, including cardiovascular health, e.g., by reducing potential for systemic infection via the oral tissues.

2.51 Any preceding composition, wherein the composition has enhanced stannous ion stability (e.g., compared to a composition comprising soluble stannous and soluble zinc compounds).

Any amount of the insoluble zinc compound that is effective for providing any of the other benefits described herein can be employed. Examples of suitable amounts of zinc compound may range from 0.05 to 5% by weight, such as from 0.1 to 4% by weight, or from 0.5 to 3% by weight, or from 0.5 to 2% by weight, or from 0.8 to 1.5% by weight, or from 0.9 to 1.1% by weight, or about 1% by weight, relative to the weight of the oral care composition.

Examples of suitable amounts of insoluble stannous compound may range from 0.01% to 5% by weight, relative to the weight of the oral care composition, for example, from 0.05 to 4% by weight, or from 0.1% to 3% by weight, or from 0.2 to 2% by weight, or from 0.3 to 1% by weight, or from 0.4 to 0.8% by weight, or from 0.4 to 0.6% by weight, or from 0.4 to 0.5% by weight, or about 0.45% by weight (e.g., 0.454%), relative to the total weight of the dentifrice composition.

The combination of zinc and stannous ions provides one or more of the following benefits: improved antimicrobial benefits compared to the zinc or stannous ions alone; improved control of plaque and/or gingivitis; and reduced malodor.

Stannous fluoride is generally considered unstable in water due to the hydrolytic and oxidative loss of stannous ions at typical pH ranges employed in oral care compositions. Consequently, stannous fluoride is generally employed in compositions containing no water or low water, or with a chelating agent. Tedious procedures are employed in order to provide stable solutions in which the tendency of the stannous ion to be oxidized or hydrolyzed is inhibited. Applicants have surprisingly found that the use of insoluble zinc and insoluble stannous in combination in a single-phase formulation may provide the same or better antibacterial and rheological benefits as provided by the use of other stannous or zinc compounds in low water compositions.

The compositions may optionally comprise additional ingredients suitable for use in oral care compositions. Examples of such ingredients include active agents, such as a fluoride source and/or a phosphate source. The compositions may be formulated in a suitable dentifrice base, e.g., comprising abrasives, e.g., silica abrasives, surfactants, foaming agents, vitamins, polymers, enzymes, humectants, thickeners, additional antimicrobial agents, preservatives, flavorings, colorings, and/or combinations thereof. Examples of suitable dentifrice bases are known in the art. Alternatively, the compositions may be formulated as a gel (e.g., for use in a tray), chewing gum, lozenge or mint. Examples of suitable additional ingredients that can be employed in the compositions of the present disclosure are discussed in more detail below.

Anionic Polymer: The compositions of the disclosure may include an anionic polymer, for example, in an amount of from 1 to 20%, e.g., from 5 to 20%, or from 8 to 15%, or from 10 to 14%, or from 11 to 13%, or about 12%. Suitable anionic polymers include synthetic anionic polymeric polycarboxylates, polyacrylic acids and polyacrylates, polyphosphonic acids, and cross-linked carboxyvinyl copolymers. Examples of synthetic anionic polymeric polycarboxylates include 1:4 to 4:1 copolymers of maleic anhydride or acid with another polymerizable ethylenically unsaturated monomer, preferably methyl vinyl ether/maleic anhydride or acid having a molecular weight (M.W.) of from 30,000 to 1,000,000, such as from 300,000 to 800,000. These copolymers are available for example as Gantrez, e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. Other suitable polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of from 1,000 to 2,000,000.

Active Agents: The compositions of the disclosure may comprise various other agents that are active to protect and enhance the strength and integrity of the enamel and tooth structure and/or to reduce bacteria and associated tooth decay and/or gum disease or to provide other desired benefits. Effective concentration of the active ingredients used herein will depend on the particular agent and the delivery system used. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product.

Compositions of the disclosure may contain from 0.1 to 1 wt % of an antibacterial agent, such as about 0.3 wt. %. Any suitable antimicrobial actives can be employed.

Fluoride Ion Source: The oral care compositions can include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al, the disclosure of each of which is hereby incorporated by reference in their entirety. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes sodium fluoride, sodium monofluorophosphate as well as mixtures thereof. In certain embodiments, the oral care composition of the disclosure may contain stannous fluoride and any additional source of fluoride ions or fluorine-providing agents in amounts sufficient to supply, in total, from 25 ppm to 25,000 ppm (mass fraction) of fluoride ions, generally at least 500 ppm, e.g., from 500 to 2000 ppm, e.g., from 1000 to 1600 ppm, e.g., about 1450 ppm. The appropriate level of fluoride will depend on the particular application. A toothpaste for general consumer use would typically have from 1000 to about 1500 ppm, with pediatric toothpaste having somewhat less. A dentifrice or coating for professional application could have as much as 5,000 or even about 25,000 ppm fluoride. Additional fluoride ion sources may be added to the compositions of the disclosure at a level of from 0.01 wt. % to 10 wt. % in one embodiment or from 0.03 wt. % to 5 wt. %, and in another embodiment from 0.1 wt. % to 1 wt. % by weight of the composition. As discussed above, weights of fluoride salts to provide the appropriate level of fluoride ion will vary based on the weight of the counterion in the salt.

Abrasives: The compositions of the disclosure can include abrasives. Examples of suitable abrasives include silica abrasives, such as standard cleaning silicas, high cleaning silicas or any other suitable abrasive silicas. Additional examples of abrasives that can be used in addition to or in place of the silica abrasives include, for example, a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Silica abrasive polishing materials useful herein, as well as the other abrasives, generally have an average particle size ranging between 0.1 and 30 microns, such as between 5 and 15 microns. The silica abrasives can be from precipitated silica or silica gels, such as the silica xerogels described in U.S. Pat. No. 3,538,230, to Pader et al. and U.S. Pat. No. 3,862,307, to Digiulio, the disclosures of which are incorporated herein by reference in their entireties. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, the disclosure of which is incorporated herein by reference in its entirety. In certain embodiments, abrasive materials useful in the practice of the oral care compositions in accordance with the disclosure include silica gels and precipitated amorphous silica having an oil absorption value of less than 100 cc/100 g silica, such as from 45 cc/100 g to 70 cc/100 g silica. Oil absorption values are measured using the ASTA Rub-Out Method D281. In certain embodiments, the silicas are colloidal particles having an average particle size of from 3 microns to 12 microns, and from 5 to 10 microns. Examples of low oil absorption silica abrasives useful in the practice of the disclosure are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging from 7 to 10 microns in diameter, and an oil absorption of less than 70 cc/100 g of silica is an example of a low oil absorption silica abrasive useful in the practice of the present disclosure.

Any suitable amount of silica abrasive can be employed. Examples of suitable amounts include 10 wt. % or more dry weight of silica particles, such as from 15 wt. % to 30 wt. % or from 15 wt. % to 25 wt. %, based on the total weight of the composition.

Foaming agents: The oral care compositions of the disclosure also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care compositions of the present disclosure. Polyoxyethylene is also commonly known as polyethylene glycol ("PEG") or polyethylene oxide. The polyoxyethylenes suitable for compositions of the present disclosure may have a molecular weight of from 200,000 to 7,000,000. In one embodiment the molecular weight may be from 600,000 to 2,000,000 and in another embodiment from 800,000 to 1,000,000. Polyox® is the trade name for the high molecular weight polyoxyethylene produced by Union Carbide. The foaming agent, (e.g., polyoxyethylene) may be present in an amount of from 0.1% to 50%, in one embodiment from 0.5% to 20% and in another embodiment from 1% to 10%, or from 2% to 5% by weight of the oral care compositions of the present disclosure.

Surfactants: The compositions useful in the compositions of the present disclosure may contain anionic surfactants, for example:
  i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
  ii. higher alkyl sulfates, such as sodium lauryl sulfate,
  iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate $(CH_3(CH_2)_{10}CH_2(OCH_2CH_2)_2OSO_3Na)$,
  iv. higher alkyl aryl sulfonates such as sodium dodecyl benzene sulfonate (sodium lauryl benzene sulfonate),
  v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In certain embodiments, the anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate, sodium lauroyl sarcosinate and sodium coconut monoglyceride sulfonates are examples of anionic surfactants of this type. In particular embodiments, the anionic surfactant is selected from sodium lauryl sulfate and sodium ether lauryl sulfate. In a particular embodiment, the compositions of the disclosure comprise sodium lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. In one embodiment, the anionic surfactant is present in a toothpaste at from 0.3% to 4.5% by weight, e.g., about 1.5%. The compositions of the disclosure may optionally contain mixtures of surfactants, e.g., comprising anionic surfactants and other surfactants that may be anionic, cationic, zwitterionic or nonionic. Generally, suitable surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al, the disclosures of which are incorporated herein by reference in their entireties.

The surfactant or mixtures of compatible surfactants that are included in addition to the anionic surfactants can be present in the compositions of the present disclosure in from 0.1% to 5.0%, in another embodiment from 0.3% to 3.0% and in another embodiment from 0.5% to 2.0% by weight of the total composition. These ranges do not include the anionic surfactant amounts.

In some embodiments, the compositions of the present disclosure include a zwitterionic surfactant, for example a betaine surfactant, for example cocamidopropyl betaine, e.g. in an amount of from 0.1% to 4.5% by weight, e.g. from 0.5 to 2% by weight cocamidopropyl betaine.

Tartar control agents: In various embodiments of the present disclosure, the compositions comprise an anti-calculus (tartar control) agent. Suitable anti-calculus agents include, without limitation, phosphates and polyphosphates (for example pyrophosphates and tripolyphosphates), polyaminopropanesulfonic acid (AMPS), hexametaphosphate salts, zinc citrate trihydrate, polypeptides, polyolefin sulfonates, polyolefin phosphates, and diphosphonates. The compositions of the disclosure thus may comprise phosphate salts in addition to the zinc phosphate. In particular embodiments, these salts are alkali phosphate salts, e.g., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; and dimeric phosphates such as pyrophosphates; and multimeric phosphates, such as tripolyphosphates, tetraphosphates, hexaphosphates and hexametaphosphates (e.g., sodium hexametaphosphate). In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions may comprise tetrasodium pyrophosphate in an amount of from 0.5 to 5% by weight, e.g., 1-3%, or 1-2% or about 2% by weight of the composition. In another embodiment, the compositions may comprise a mixture of tetrasodium pyrophosphate (TSPP) and sodium tripolyphosphate (STPP), e.g., in proportions of TSPP at from 0.5 to 5 wt. %, such as from 1 to 2 wt. % and STPP at from 0.5% to 6 wt. %, such as 1 to 4%, or 2 to 3% by weight of the composition. Such phosphates are provided in an amount effective to aid in cleaning the teeth, and/or to reduce tartar buildup on the teeth, for example in an amount of from 0.2 to 20 wt. %, e.g., from 1 to 15 wt. %, by weight of the composition.

Flavoring Agents: The oral care compositions of the disclosure may also include a flavoring agent. Flavoring agents which are used in the practice of the present disclosure include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of from 0.1 to 5% by weight e.g., from 0.5 to 1.5% by weight.

Other Polymers: The oral care compositions of the disclosure may also include additional polymers to adjust the viscosity of the formulation or enhance the solubility of other ingredients. Such additional polymers include polyethylene glycols, polysaccharides (e.g., cellulose derivatives, for example carboxymethyl cellulose, hydroxymethyl cellulose, ethyl cellulose, microcrystalline cellulose or polysaccharide gums, for example xanthan gum, guar gum or carrageenan gum). Acidic polymers, for example polyacrylate gels, may be provided in the form of their free acids or partially or fully neutralized water-soluble alkali metal (e.g., potassium and sodium) or ammonium salts. In one embodiment, the oral care composition may contain PVP. PVP generally refers to a polymer containing vinylpyrrolidone (also referred to as N-vinylpyrrolidone, N-vinyl-2-pyrrolidione and N-vinyl-2-pyrrolidinone) as a monomeric unit. The monomeric unit consists of a polar imide group, four non-polar methylene groups and a non-polar methane group.

In some embodiments, the compositions of the disclosure comprise one or more polyethylene glycols, for example, polyethylene glycols in a molecular weight range from 200 to 800. For example, the compositions may comprise one or more of polyethylene glycol 200, polyethylene glycol 300, polyethylene glycol 400, polyethylene glycol, 600 or polyethylene glycol 800.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of from 0.5% to 5.0% by weight of the total composition are used.

Humectants: Within certain embodiments of the oral compositions, it is also desirable to incorporate a humectant to prevent the composition from hardening upon exposure to air. Certain humectants can also impart desirable sweetness or flavor to dentifrice compositions. Suitable humectants include edible polyhydric alcohols such as glycerin, sorbitol, xylitol, propylene glycol as well as other polyols and mixtures of these humectants. In one embodiment of the disclosure, the principal humectant is one of glycerin, sorbitol or a combination thereof. The humectant may be present at levels of greater than 15 wt. %, such as from 15 wt. % to 55 wt. %, or from 20 wt. % to 50 wt. %, or from 20 wt. % to 40 wt. %, or about 20% or about 30% or about 40%, based on the total weight of the composition.

Other optional ingredients: In addition to the above-described components, the embodiments of this disclosure can contain a variety of optional oral care ingredients some of which are described below. Optional ingredients include, for example, but are not limited to, adhesives, sudsing agents, flavoring agents, sweetening agents such as sodium saccharin, additional antiplaque agents, abrasives, aesthetics such as $TiO_2$ coated mica or other coloring agents, such as dyes and/or pigments.

In some embodiments, the oral care compositions of the present disclosure are either essentially free of, free of, or do not include any sodium hexametaphosphate. In some embodiments, the oral care compositions of the present disclosure are either essentially free of, free of, or do not include any halogenated diphenyl ethers (e.g., triclosan).

By "essentially free" is meant that the compositions have no more than 0.01% by weight of these compounds.

In some embodiments, the compositions of the present disclosure are either essentially free of, free of or do not include any complexing agents for increasing solubility of zinc phosphate and/or for maintaining the stannous fluoride in solution. Examples of known complexing agents that can be excluded from the compositions of the present disclosure include the chelating agents taught in U.S. Patent Application No. 2007/0025928, the disclosure of which is hereby incorporated by reference in its entirety. Such chelating agents include mineral surface-active agents, including mineral surface-active agents that are polymeric and/or polyelectrolytes and that are selected from phosphorylated polymers, wherein if the phosphorylated polymer is a polyphosphate, the polyphosphate has average chain length of 3.5 or more, such as 4 or more; polyphosphonates; copolymers of phosphate- or phosphonate-containing monomers or polymers with ethylenically unsaturated monomers, amino acids, proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate) and poly(vinyl benzyl chloride); and mixtures thereof. Other known complexing agents that can be excluded from the compositions of the present disclosure include those taught in CA 2634758, the disclosure of which is incorporated here by reference in its entirety. Examples include polyphosphorylated inositol compounds such as phytic acid, myo-inositol pentakis(dihydrogen phosphate); myo-inositol tetrakis(dihydrogen phosphate), myo-inositol trikis(dihydrogen phosphate), and alkali metal, alkaline earth metal or ammonium salts of any of the above inositol compounds. Phytic acid is also known as myo-inositol 1,2,3,4,5,6-hexakis (dihydrogen phosphate) or inositol hexaphosphoric acid.

In another aspect, the present disclosure provides a method of treatment or prevention of gingivitis, plaque, and/or dental caries, the method comprising the application to the oral cavity of a person in need thereof a composition according to the invention (e.g., Composition 1.0 et seq), e.g., by brushing, for example, one or more times per day.

In another aspect, the present disclosure provides a method of using the compositions described herein (e.g., any of Compositions 1.0 et seq) to increase zinc levels in the enamel.

The methods comprise applying any of the compositions as described herein to the teeth, e.g., by brushing, or otherwise administering the compositions to the oral cavity of a subject in need thereof. The compositions can be administered regularly, such as, for example, one or more times per day. In various embodiments, administering the compositions of the present disclosure to a patient can provide one or more of the following benefits: (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing and/or malodor producing bacteria, (viii) increase relative levels of arginolytic bacteria, (ix) reduce or inhibit formation of dental caries, (x) reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) whiten teeth; (xiv) reduce tartar build-up, (xv) reduce or prevent oral malodor, and/or (xvi) promote systemic health, including cardiovascular health, e.g., by reducing potential for systemic infection via the oral tissues. The disclosure further provides compositions for use in any of the above methods. Further embodiments provide methods wherein at least one tooth is remineralized after administration of a composition as described herein.

The present application further discloses methods of making any of the compositions of the present disclosure. In particular three methods are provided herein. In a first embodiment, the present disclosure provides a method of making an oral care composition, e.g. a high-water oral care composition, comprising combining a soluble stannous compound and/or a soluble zinc compound with a precipitating agent, as described herein, in an aqueous mixture (e.g., a aqueous solution), for a sufficient amount of time to form an insoluble stannous compound and/or an insoluble zinc compound; and subsequently, incorporating the insoluble stannous compound and/or insoluble zinc compound (either as the aqueous solution or in purified [e.g., dried, evaporated or lyophilized] form) into an oral care composition, e.g., by adding it to an oral care composition or combining it with other oral care ingredients. In second embodiment, the present disclosure provides a method of making an oral care composition, e.g., a high-water oral care composition, comprising combining a soluble stannous compound and/or a soluble zinc compound with one or more additional oral care ingredients to form an oral care composition (or oral care intermediate composition) and subsequently adding a water-soluble base in a suitable amount to raise the pH of the composition above 7.0 (e.g., to 7.0 to 9.0, or 7.0 to 8.5, or 7.0 to 8.0, or 7.0 to 7.5) causing the precipitation of stannous compound and/or zinc compound in the composition. In third embodiment, the present disclosure provides a method of making an oral care composition, e.g., a high-water oral care composition, comprising combining an insoluble stannous compound and an insoluble zinc compound with one or more additional oral care ingredients to form an oral care composition, e.g., without the use of any soluble stannous or soluble zinc compounds to form the insoluble stannous and insoluble zinc compounds. In some embodiments, these methods provide enhanced stannous ion stability (e.g., compared to a composition comprising soluble stannous and soluble zinc compounds). In some embodiments, these methods are methods of enhancing stannous ion stability in an oral care composition (e.g., a high-water oral care composition).

The amount of water and of any additional ingredients employed in these methods may be any of the amounts and ingredients recited herein for the compositions of the present disclosure. Any standard mixing techniques can be employed to combine the ingredients.

EXAMPLES

Example 1—Dentifrice Formulations

Representative Dentifrice Formulations according to the present disclosure are prepared according to Table 1 below:

TABLE 1

| Ingredient | Weight % |
| --- | --- |
| Water | Q.S. (e.g., 15-40) |
| Humectants | 15-55 |

TABLE 1-continued

| Ingredient | Weight % |
| --- | --- |
| Abrasives | 10-30 |
| Thickeners | 0.5-5 |
| Anionic Polymer | 0-20 |
| Soluble or insoluble zinc compound* | 0.05-10 |
| Soluble or insoluble stannous compound* | 0.05-10 |
| Flavor, Sweetener, Colors | 0.5-5 |
| Alkali Phosphate Salts | 0.5-5 |
| Anionic Surfactant | 0-10 |
| Other Surfactant | 0.1-4.5 |
| Soluble base* | 0.0-10.0 |
| Precipitating Agent* | 0.0-10.0 |
| Fluoride source (e.g., soluble fluoride) | 0.5-10 |

*Provided that if a soluble zinc compound or soluble stannous compound is used, then a sufficient amount of precipitating agent or soluble base is added to provide at least 70% insoluble stannous and 70% insoluble zinc in the final composition.

Experimental formulations (Examples A to E) according to the present disclosure are prepared as shown in Table 2, each comprising the insoluble zinc compound zinc oxide. Comparative composition (Example F) is also shown in Table 2. Comparative compositions (Examples G to I) are not shown in Table 2 as they are commercial products containing both stannous and zinc salts. Comparative composition G is a commercial, high-water, anti-caries, anti-plaque, and anti-gingivitis dentifrice containing stannous fluoride, stannous chloride, and zinc citrate, and sodium hydroxide. Comparative composition H is a commercial, low water, anti-caries, anti-plaque, and anti-gingivitis dentifrice containing stannous fluoride, zinc lactate, and sodium hexametaphosphate. Comparative Composition I is a commercial, low-water, anti-caries, anti-plaque, and anti-gingivitis dentifrice containing stannous fluoride, stannous chloride, zinc citrate, and sodium hexametaphosphate. Ingredients in Table 2 are listed by weight percent of the composition. The compositions of Example A to C and Example E are prepared by combining the soluble stannous compound with the precipitating agent in aqueous solution to form an insoluble stannous compound, followed by addition of the other oral care ingredients. The composition of Example D is prepared by combining all ingredients other than the soluble base together then adding the soluble base to raise the pH above 7.0, resulting in precipitation of insoluble stannous compound.

TABLE 2

| Ingredient | A | B | C | D | E | F |
| --- | --- | --- | --- | --- | --- | --- |
| Stannous Fluoride | 0.45 | 0.45 | 0.45 | 0.45 | 0.45 | 0.45 |
| Stannous Chloride Dihydrate | 1.1 | 0.65 | 0.65 | 1.1 | 1.1 | |
| Stannous Pyrophosphate | | | | | | 1 |
| Alkali phosphate | 1.75 | 1.50 | | 1.74 | 1.75 | 1 |
| Tetrasodium Pyrophosphate | | | | | 0.5 | 2 |
| Flavor, Sweetener, Colors | 1.85 | 2.35 | 2.25 | 2.25 | 1.85 | 2.2 |
| Water | Q.S. (e.g., ~25%) | Q.S. (e.g., ~20%) | Q.S. (e.g., ~31%) | Q.S. (e.g., ~19%) | Q.S. (e.g., ~27%) | Q.S. (e.g., ~9%) |
| Anionic Polymer | 1.3 | 1.3 | 1.3 | 0.85 | 1.3 | 0.3 |
| Non-ionic polymer | 3 | | | | 3 | |
| Humectant | 26 | 38 | 28 | 37 | 26 | 45 |
| Sodium Hydroxide (50%) | 0.4 | 0.5 | 0.5 | 0.66 | 0.24 | |
| 37.5% sodium silicate solution | 2 | | | | | |

TABLE 2-continued

| Ingredient | A | B | C | D | E | F |
|---|---|---|---|---|---|---|
| Zinc Oxide | 1.2 | 1.2 | 1.2 | 1.2 | 1.2 | 1.0 |
| Silica | 23 | 20 | 26 | 22 | 23 | 24 |
| Anionic Surfactant | 1.5 | 2 | 2 | 2 | 1.5 | 2 |
| Zwitterionic Surfactant | 0.5 | | | 1.25 | 0.5 | 1 |
| Preservative | | 0.5 | | | | |

Example 2—Stannous and Zinc Ion Concentration

The nine dentifrice compositions shown above are compared in stannous and zinc ion concentration.

The following method is used to determine the concentration of soluble stannous and soluble zinc in the final dentifrice compositions: 1.00 grams of dentifrice is homogeneously dispersed in 100 mL of deionized water. An aliquot of the dispersion is centrifuged for 15 minutes at 3,000 rpm. After centrifugation, an aliquot of the supernatant is analyzed for total stannous content and total zinc content using atomic absorption spectrophotometry. The results are shown in Table 3 below.

TABLE 3

| | Total Stannous | Soluble Stannous | Percent Soluble Stannous | Total Zinc | Soluble Zinc | Percent Soluble Zinc |
|---|---|---|---|---|---|---|
| Ex. A | 9200 | 1200 | 13% | 9600 | 300 | 3% |
| Ex. B | 6900 | 1100 | 16% | 9200 | 700 | 8% |
| Ex. C | 6900 | 1100 | 16% | 9200 | 800 | 9% |
| Ex. D | 9200 | 1000 | 11% | 9200 | 200 | 2% |
| Ex. E | 9200 | 1500 | 16% | 9200 | 800 | 9% |
| Ex. F | 9200 | 6200 | 67% | 9600 | 6100 | 64% |
| Ex. G | 6500 | 800 | 12% | 1800 | 1500 | 83% |
| Ex. H | 3200 | 1800 | 56% | 6800 | 6000 | 88% |
| Ex. I | 6600 | 4400 | 67% | 5000 | 4900 | 98% |

In all prototype dentifrices, the soluble stannous and zinc concentrations are found to be less than 30% of the total stannous and zinc concentrations. Comparative composition G is found to have little soluble stannous ion, despite being formulated with soluble stannous chloride and fluoride. Comparative compositions H and I are found to have high concentrations of soluble stannous. Each of comparative compositions G, H and I are found to have high concentrations of soluble zinc.

Example 3: Fluoride Stability

The stability of ionic fluoride can be expressed as percent retention (concentration of active ingredient of an aged sample divided by its initial value). The following method is used to determine the concentration of soluble ionic fluoride: 10.0 grams of dentifrice is homogeneously dispersed in 100 mL of deionized water. An aliquot of the dispersion is centrifuged for 15 minutes at 12,000 rpm. After centrifugation, an aliquot of the supernatant is analyzed for ionic fluoride using a calibrated fluoride ion selective electrode. The results are shown in Table 4 below.

TABLE 4

| | Initial Fluoride Concentration | Fluoride Concentration at 8 Weeks | Fluoride Retention |
|---|---|---|---|
| Ex. A | 1100 ppm | 986 ppm | 90% |
| Ex. B | 1100 ppm | 1001 ppm | 91% |
| Ex. C | 1100 ppm | 983 ppm | 89% |
| Ex. D | 1100 ppm | 949 ppm | 86% |
| Ex. E | 1100 ppm | 1006 ppm | 91% |
| Ex. F | 1100 ppm | 902 ppm | 82% |

As shown in Table 4, the composition according to the present disclosure demonstrate superior ionic fluoride retention compared to the comparative composition of Example F, which contains high relative percentages of soluble stannous and soluble zinc.

Example 4: Viscosity

An 8-week stability study is performed to determine rheological stability. The following method is used to determine the viscosity of each dentifrice: 20.0 g of dentifrice is dispensed into a suitable vessel. Using a Brookfield DVIII-Ultra viscometer with a V-74 spindle vane, the viscosity at 1 rpm is measured. The results are shown in Table 5 below.

TABLE 5

| | Initial Viscosity (cps) | Viscosity at 8 Weeks (cps) |
|---|---|---|
| Ex. A | 355,830 | 326,276 |
| Ex. B | 267,305 | 195,140 |
| Ex. C | 297,176 | 317,475 |
| Ex. D | 376,136 | 257,989 |
| Ex. E | 315,603 | 459,783 |

As shown in Table 5, the compositions according to the present disclosure provide stable viscosity upon aging.

Example 5: Antibacterial Efficacy

The antibacterial efficacy of the composition of Example D is evaluated compared to comparative Example E using the pH-stat method. See G. K. Watson & F. J. G. van der Ouderaa, Inhibition of Acid Production by *Streptococcus mutans* NCTC 10449 by Zinc and the Effect of Metal Speciation, Caries Research, 25: 431-437 (1991). The results are shown in Table 6 below.

| Dosage | Example D: Average Reduction (%) | Example F: Average Reduction (%) |
|---|---|---|
| 0 ppm | — | — |
| 67 ppm | 42.69 ± 0.55 | 46.03 ± 1.23 |
| 333 ppm | 79.73 ± 1.91 | 61.07 ± 1.29 |
| 667 ppm | 97.14 ± 1.90 | 72.08 ± 0.65 |

The results show that at a dentifrice concentration of 667 ppm, the Example D composition reduces the metabolic activity of *Streptococcus mutans* by more than 97%. In contrast, the comparative composition E, which contains the same concentration of total stannous and total zinc, only reduces the metabolic activity by approximately 70%.

While the present invention has been described with reference to embodiments, it will be understood by those skilled in the art that various modifications and variations may be made therein without departing from the scope of the present invention as defined by the appended claims.

The invention claimed is:

1. An oral care composition comprising an orally acceptable carrier, stannous fluoride and/or stannous chloride, an insoluble stannous compound selected from stannous phosphate and stannous hydroxide or a mixture thereof, and an insoluble zinc compound, wherein the insoluble zinc compound is zinc oxide, wherein the composition comprises less than 30% soluble stannous as a fraction of total stannous by weight, and less than 30% soluble zinc as a fraction of total zinc by weight, and
wherein the insoluble stannous compound is formed during manufacture of the composition by combining the stannous fluoride and/or stannous chloride with a precipitating agent selected from an alkali metal phosphate, an alkali metal hydroxide, or a combination thereof, in an aqueous solution prior to the addition of any other ingredients of the composition;
and wherein the composition is formed by combining the stannous fluoride and/or stannous chloride and the precipitating agent or agents in a 0.5:1 to 2:1 molar ratio, measured by the molar amount of stannous ion to precipitating anion.

2. The composition according to claim 1, wherein the composition is a high-water oral care composition.

3. The composition according to claim 1, wherein the composition further comprises an additional insoluble zinc compound selected from one or more of zinc phosphate, zinc pyrophosphate, zinc silicate, zinc oleate, zinc hydroxide, zinc carbonate, zinc peroxide and zinc sulfide.

4. The composition according to claim 1, wherein the composition further comprises an additional insoluble stannous compound selected from one or more of stannous pyrophosphate, stannous oxide, stannous sulfate, and stannous peroxide.

5. An oral care composition made by combining stannous fluoride and/or stannous chloride with a precipitating agent selected from an alkali metal phosphate, an alkali metal hydroxide, or a combination thereof, in an aqueous solution, to form an insoluble stannous compound, and further combining this pre-mix with an insoluble zinc compound and any other oral care ingredients;
wherein the composition comprises less than 30% soluble stannous as a fraction of total stannous by weight, and less than 30% soluble zinc as a fraction of total zinc by weight, and wherein the composition is formed by combining the stannous fluoride and/or stannous chloride and the precipitating agent or agents in a 0.5:1 to 2:1 molar ratio, measured by the molar amount of stannous ion to precipitating anion.

6. The composition according to claim 5, wherein the insoluble zinc compound is selected from one or more of zinc oxide, zinc phosphate, zinc pyrophosphate, zinc silicate, zinc oleate, zinc hydroxide, zinc carbonate, zinc peroxide and zinc sulfide.

7. The composition according to claim 5, wherein the insoluble stannous compound is selected from one or more of stannous phosphate, and stannous hydroxide.

8. The composition according to claim 1, wherein the composition comprises the insoluble zinc compound in an amount of from 0.05 to 10% by weight, relative to the weight of the oral care composition.

9. The composition according to claim 1, wherein the composition comprises the insoluble stannous compound in an amount of from 0.05 to 10% by weight, relative to the weight of the oral care composition.

10. A composition according to claim 1, wherein the amount of the water is 10% by weight or more, relative to the weight of the oral care composition.

11. The composition according to claim 1, wherein the composition comprises less than 30% soluble stannous by weight of total stannous.

12. The composition according to claim 1, wherein the composition comprises less than 30% soluble zinc by weight of total zinc.

13. The composition according to claim 1, wherein the composition further comprises a polymeric rheological modifier.

14. The composition according to claim 13, wherein the anionic polymer is selected from the group consisting of synthetic anionic polymeric polycarboxylates, polyacrylic acids, polyphosphonic acids, and cross-linked carboxyvinyl copolymers.

15. The composition according to claim 14, wherein the composition comprises an anionic polymeric polycarboxylate, optionally wherein the anionic polymeric polycarboxylate is selected from a modified cellulose polymer or a gum.

16. The composition according to claim 13, wherein the polymeric rheological modifier is present in an amount of 1 to 20% by weight of the composition.

17. The composition according to claim 1, wherein the oral care composition is a dentifrice, powder, cream, strip or gum.

18. A method of treatment of gingivitis, plaque, and/or dental caries, the method comprising the application to the oral cavity of a person in need thereof a composition according to claim 1.

19. The composition according to claim 1, wherein the composition is formed by combining the stannous fluoride and/or stannous chloride and the precipitating agent or agents in a 0.5:1 to 1:1 molar ratio.

20. The composition of claim 19, wherein the precipitating agents are selected from sodium hydroxide, potassium hydroxide, sodium phosphate, potassium phosphate, or a combination thereof.

* * * * *